United States Patent
Case et al.

(10) Patent No.: US 9,855,299 B2
(45) Date of Patent: *Jan. 2, 2018

(54) METHODS AND COMPOSITIONS FOR TREATMENT OF RETINAL DEGENERATION

(71) Applicant: SanBio, Inc., Mountain View, CA (US)

(72) Inventors: Casey C. Case, San Mateo, CA (US); Toru Kawanishi, Kyoto (JP); Noriyuki Kuno, Tokyo (JP)

(73) Assignee: SanBio, Inc., Mountain View, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/076,378

(22) Filed: Mar. 21, 2016

(65) Prior Publication Data

US 2016/0271181 A1   Sep. 22, 2016

Related U.S. Application Data

(63) Continuation of application No. 13/801,453, filed on Mar. 13, 2013, now Pat. No. 9,326,999.

(60) Provisional application No. 61/711,665, filed on Oct. 9, 2012.

(51) Int. Cl.
| | |
|---|---|
| *A61K 48/00* | (2006.01) |
| *A61K 35/28* | (2015.01) |
| *C12N 5/10* | (2006.01) |
| *A61K 9/00* | (2006.01) |
| *A61K 35/12* | (2015.01) |

(52) U.S. Cl.
CPC ............ *A61K 35/28* (2013.01); *A61K 9/0048* (2013.01); *C12N 5/10* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 6,989,271 B2 | 1/2006 | Dezawa et al. | |
| 7,682,825 B2 | 3/2010 | Dezawa et al. | |
| 8,092,792 B2 | 1/2012 | Dezawa et al. | |
| 8,133,725 B2 | 3/2012 | Dezawa et al. | |
| 8,361,456 B2 | 1/2013 | Dezawa et al. | |
| 8,785,190 B2 | 7/2014 | Dao et al. | |
| 9,326,999 B2 | 5/2016 | Case et al. | |
| 2010/0266554 A1 | 10/2010 | Mori et al. | |
| 2010/0310529 A1 | 12/2010 | Aizman | |
| 2011/0138114 A1 | 6/2011 | Case | |

(Continued)

FOREIGN PATENT DOCUMENTS

| | | |
|---|---|---|
| WO | WO 2008/102460 | 8/2008 |
| WO | WO 2009/023251 | 2/2009 |

(Continued)

OTHER PUBLICATIONS

Aizman et al. "Quantitative Microplate Assay for Studying Mesenchymal Stromal Cellinduced Neuropoiesis," Stem Cells Translational Medicine, 2.:223-232 (2013).

(Continued)

*Primary Examiner* — Qian Janice Li
(74) *Attorney, Agent, or Firm* — Levine Bagade Han LLP

(57) ABSTRACT

Disclosed herein axe methods and compositions for treating retinal degeneration, such as occurs in retinitis pigmentosa and age-related macular degeneration, using descendents of marrow adherent stem cells that have been engineered to express an exogenous Notch intracellular domain.

18 Claims, 10 Drawing Sheets

(56) References Cited

U.S. PATENT DOCUMENTS

| | | |
|---|---|---|
| 2011/0229442 A1 | 9/2011 | Dezawa |
| 2011/0306137 A1 | 12/2011 | Aizman |
| 2012/0263681 A1 | 10/2012 | Miyoshi et al. |
| 2013/0071924 A1 | 3/2013 | Dezawa |
| 2013/0095084 A1 | 4/2013 | Dao et al. |
| 2013/0195817 A1 | 8/2013 | Dao et al. |
| 2013/0210000 A1 | 8/2013 | Aizman et al. |
| 2014/0099291 A1 | 4/2014 | Case et al. |
| 2014/0186316 A1 | 7/2014 | Borlongan et al. |
| 2014/0219976 A1 | 8/2014 | Case et al. |
| 2014/0286918 A1 | 9/2014 | Dao et al. |

FOREIGN PATENT DOCUMENTS

| | | |
|---|---|---|
| WO | WO 2009/071659 | 6/2009 |
| WO | WO 2009/134409 | 11/2009 |
| WO | WO 2011/106783 | 9/2011 |
| WO | WO 2012/012803 | 1/2012 |
| WO | WO 2014/058464 | 4/2014 |

OTHER PUBLICATIONS

Aizman et al., "Extracellular Matrix Produced by Bone Marrow Stromal Cells and by Their Derivatne, SB623 Cells, Supports Neural Cell Growth," J Neurosci. Res. 87(14):3198-3206 (2009).

Ali et al., "Notch-Induced Human Bone Marrow Stromal Cell Grafts Express Neuronal Phenotypic Markers and Reduce Ischemic Cell Loss in Tandem With Behavioral Recovery of Transplanted Stroke Animals," Cell Transplantation, 17:458 (2008).

Bonnet et al., "Usher Syndrome (Sensorineural Deafness and Retinitis Pigmentosa): Pathogenesis, Molecular Diagnosis and Therapeutic Approaches." Curro Opin. Neural., 25(1):42-49 (2012).

Cai et al., "Oxidative Stress: The Achilles' Heel of Neurodegenerative Diseases of the Retina," Front Biosci., 17:1976-1995 (2012).

Coussea et al., "Choroideremia: A Review of General Findings and Pathogenesis," Genetics, 33(2):57-65 (2012).

Dao et al., "Comparing the Angiogenic Potency of Naive Marrow Stromal Cells and Notch-Transfected Marrow Stromal Cells," J Translational Medicine, 11:81-91 (2013).

Dao et al., "Comparing the Immunosuppressive Potency of Naive Marrow Stromal Cells and Notch-Transfected Marrow Stromal Cells," J Neuroinflammation, 8:133-146 (2011).

D'Cruz et al., "Mutation of the Receptor Tyrosine Kinase Gene Mertk in the Retinal Dystrophic RCS RAT," Human Molecular Genetics, 2(1):645-651 (2000).

Del Amo, F. et al., "Cloning, Analysis and Chromosomal Localization of Notch-I, A Mouse Homolog of *Drosophilia* Notch," Genomics, 12:259-264 (1993).

Dezawa et al. "Sciatic Nerve Regeneration in Rats Induced by Transplantation of In Vitro Differentiated Bone-Marrow Stromal Cells," The European Journal of Neuroscience 14(11):1771-1776 (2001).

Dezawa et al., "Transdifferentiation of Bone Marrow Stromal Cells to Neural Cells and Application to Stem Cell Therapy," Acta Anatomica Nipponica 78suppl:97 (Abstract S04-6) (2003) (English translation also enclosed).

Dezawa et al., "Treatment of Neurodegenerative Diseases Using Adult Bone Marrow Stromal Cell-Derived Neurons," Expert Opinion on Biological Therapy 5(4):427-435 (2005).

Dezawa, et al., "Specific Induction of Neuronal Cells From Bone Marrow Stromal Cells and Application for Autologous Transplantation," J Clin Invest 113(12):1701-1710 (2004).

GenBank Accession No. CAB40733 (Apr. 15, 2005).

Glasvaski-Joksimovic et al., "Glial Cell Line-Derned Neurotrophic Factor-Secreting Genetically Modified Human Bone Marrow-Derned Mesenchymal Stem Cells Promote Recovery in a Rat Model of Parkinson's Disease," Cell Transplantation, I8.:801-814 (2009).

Glavaski-Joksimovic, et al., "Reversal of Dopaminergic Degeneration in a Parkinsonian Rat Following Micrografting of Human Bone Marrow-Derived Neural Progenitors," Cell Transplant 18:801-814 (2009).

Goodwin, "Hereditary Retinal Disease," Curro Opin. Ophthalmol., 19(3):255-262 (2008).

Harvey et al., "Proteomic Analysis of the Extracellular Matrix Produced by Mesenchymal Stromal Cells: Implications for Cell Therapy Mechanism," PLOS One, 8(11):e79283, Nov. 2013.

Hayase, Makoto et al., "Committed neural progenitor cells derived from genetically modified bone marrow stromal cells ameliorate deficits in a rat model of stroke," Journal of Cerebral Blood Flow & Metabolism, 29:1409-1420, 2009.

Inoue et al., "Subretinal transplantation of bone marrow mesenchymal stem cells delays retinal degeneration in the RCS rat model of retinal degeneration," Exp Eye Res, 85:234-41 (2007).

Johnson et al., "Neuroprotective Effects of Intravitreal Mesenchymal Stem Cell Transplantation in Experimental Glaucoma," Invest Ophthalmol Vis Sci, 51(4):2051-9 (Apr. 2010).

Lund et al., "Cells Isolated from Umbilical Cord Tissue Rescue Photoreceptors and Visual Functions in a Rodent Model of Tetinal Disease." Stem Cells, 25:602-11 (2007).

Mimura, Toshiro et al., "Behavioral and Histological Evaluation of a Focal Cerebral Infarction Rat Model Transplanted With Neurons Induced from Bone Marrow Stromal Cells," J. Neuropathol Exp. Neurol., vol. 64, No. 12:1108-1117, Dec. 2005.

Mumm et al., "Notch Signaling: From the Outside in," Dev. Bioi., 228 (2):151-165 (2000).

NCBI Reference Sequence No. NM_017167 (Apr. 29, 2013).

Schroeter et al., "Notch-1 Signalling Requires Ligand-Induced Proteolytic Release of Intracellular Domain" Nature, 393:382-386 (1998).

SwissProt P46531 (Nov. 1, 1995).

SwissProt QOI705 (Nov. 1, 1995).

Tajiri et al., "Stem Cell Recruitment of Newly Formed Host Cells via a Successful Seduction? Filling the Gap Between Neurogenic Niche and Injured Brain Site," PLOS One, 8(9):e74857 (2013).

Tate et al. "Transplanted Mesenchymal Stem Cells Aid the Injured Brain through Trophic Support Mechanisms," Stem Cells and Cancer Stem Cells, vol. 4, M.A. Hayat (Ed), 297-304 (2012).

Tate et al., "Human Mesenchymal Stromal Cells and Their Derivative, S8623 Cells, Rescue Neural Cells via Trophic Support Following In Vitro Ischemia," *Cell Transplantation*, vol. 19, pp. 973-984, 2010.

Tate et al., "Moving Cell Therapy From Basic Research Into the Clinic: SB823 Cells for Stroke Disability," Cell Transplantation, 20:588 (2011).

Tate et al., "Mesenchymal Stromal Cells to Treat Brain Injury," Advanced Topics in Neurological Disorders, K. S. Chen (Ed), 45-78 (2012).

Weinmaster et al., "A Homolog of *Drosophila* Notch Expressed During Mammalian Development," Development 113:199-205 (1991).

Xu et al., "Transplantation of Neuronal Cells Induced From Human Mesenchymal Stem Cells Improves Neurological Functions Afterstroke Without Cell Fusion," J. Neuroscience Research 88:3598-3609 (2010).

Yasuhara, et al., "Notch-Induced Rat and Human Bone Marrow Stromal Cell Grafts Reduce Ischemic Cell Loss and Ameliorate Behavioral Deficits in Chronic Stroke Animals," Stem Cells and Development 18:1501-1514 (2009).

Yu et al., "Effects of bone marrow stromal cell injection in an experimental glaucoma model," Biochem Biophys Res Comm, 344;1071-9 (2006).

Xu W. et al., "Mesenchymal stem cells for retinal diseases," International Journal of Ophthalmology, 4(4):413-421, Aug. 18, 2011.

Ahmad, Iqbal et al."Regulation of Ocular Angiogenesis by Notch Signaling: Implications in Neovascular Age-Related Macular Degeneration.", *Invest Ophthalmol Vis Sci.*, vol. 52(6), pp. 2868-2878 (Published on May 2011).

Huo, D. M. et al., "Differentiation of mesenchymal stem cell in the microenvironment of retinitis pigmentosa," *Int. J. Ophthalmol.*, vol. 3, No. 3, p. 216-219 (Sep. 18, 2010).

(56) References Cited

OTHER PUBLICATIONS

Nuzzi, R. et al., "Effect of In Vitro Exposure of Corticosteroid Drugs, Conventionally Used in AMD Treatment, on Mesenchymal Stem Cells," *Stem Cell Int.*, vol. 2012. Article ID 946090, p. 1-11 (May 2012).

Prockop, D. J., "Potential Therapies with Adult Stem/Progenitor Cells from Bone Marros (MSCs) and the Proteins They Produce in Response to Injuries from Injured Tissues," *FASEB J.*, vol. 26, No. 1, Suppl. 335.1 (Apr. 2012).

Tate, C. C. et al., "SB623 Cells Promote Angiogenesis—A Potential Mechanism of Action ofr Enhancing Neural Regeneration," *Cell Transplant*, vol. 21, Suppl. 1, p. 794 (Apr. 2012).

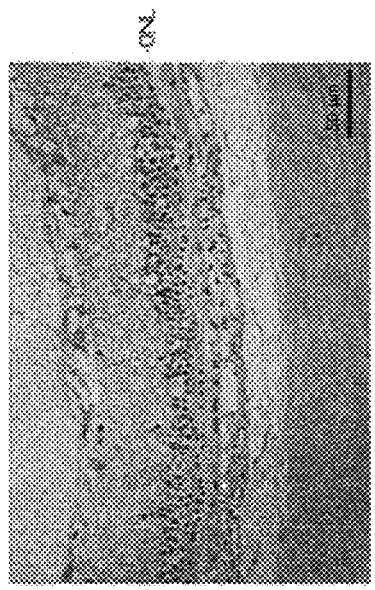
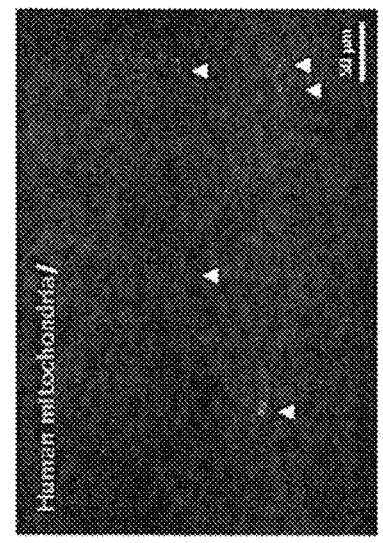
Figure 10
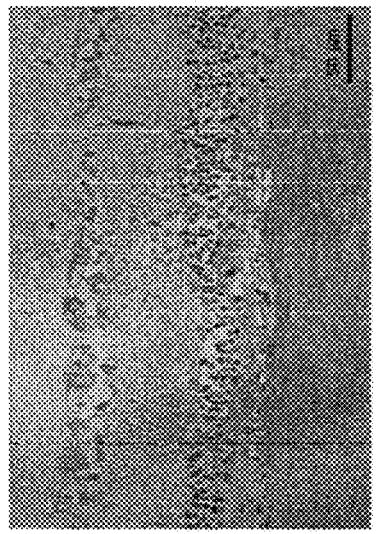
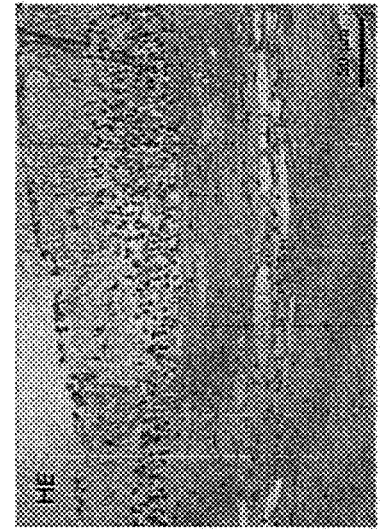
Figure 11

METHODS AND COMPOSITIONS FOR TREATMENT OF RETINAL DEGENERATION

CROSS-REFERENCE TO RELATED APPLICATIONS

This application is a continuation of U.S. patent application Ser. No. 13/801,453, filed Mar. 13, 2013 which claims the benefit of U.S. Provisional Application No. 61/711,665, filed Oct. 9, 2012, the disclosures of which re hereby incorporated by reference herein in their entirety.

STATEMENT REGARDING FEDERAL SUPPORT

Not applicable.

FIELD

The present application is in the field of cell therapies for retinal degeneration as occurs, for example, in retinitis pigmentosa and in age-related macular degeneration (AMD).

BACKGROUND

Retinal degeneration, resulting, for example, from choroidal neovascularization ("wet AMD") or from buildup of cellular debris between the retina and the choroid ("dry AMD"), is one of the major causes of blindness in the world today. Cai et al. (2012) *Front Biosci.* 17:1976-95. Similarly, degeneration and death of photoreceptor cells (rods and cones), as occurs in Retinitis pigmentosa, can also lead to deterioration and/or loss of vision. Accordingly, treatments that block and/or reverse retinal, degeneration, in particular treatments that restore photoreceptor function, are needed.

SUMMARY

Disclosed herein are methods and compositions for treating retinal degeneration, using cells descended from marrow adherent stem cells (MASCs) that have been engineered to express an exogenous Notch intracellular domain. Such cells are denoted SB623 cells for the purposes of the present disclosure.

In one aspect, disclosed herein are methods of treating retinal degeneration by administering SB623 cells to the eye of a subject in need thereof.

In another aspect, disclosed herein are methods of increasing photoreceptor activity in the eye of a subject, the methods comprising administering SB623 cells to the eye of the subject such that photoreceptor activity is increased.

In another aspect, disclosed herein are methods of enhancing photoreceptor function in the eye of a subject, the methods comprising administering SB623 cells to the eye of the subject such that photoreceptor function is enhanced.

In another aspect, disclosed herein are methods of enhancing transmission of visual signals from the retina to the visual cortex of the brain, the methods comprising administering SB623 cells to the eye of the subject such that transmission of visual signals from the retina to the visual cortex of the brain is enhanced.

In any of the methods described herein, the cells can be administered by any delivery method, including direct injection, topical administration and the like. In certain embodiments, the SB623 cells are administered as a composition (or formulation) comprising the cells, for example in combination with one or more pharmaceutical carriers. In addition, the methods can involve repeated administration of SB623 cells, in the same or different formulations.

Accordingly, the present disclosure provides, inter alia, the following embodiments:

1. A method for treating retinal degeneration in a subject in need thereof, the method comprising administering SB623 cells to the subject.
2. The method of embodiment 1, wherein SB623 cells are transplanted into the eye of the subject.
3. The method of either of embodiments 1 or 2, wherein the transplantation is intravitreal.
4. The method of either of embodiment 1 or 2, wherein the transplantation is subretinal.
5. The method of any of embodiments 1-4, wherein the retinal degeneration occurs in retinitis pigmentosa.
6. The method of any of embodiments 1-4, wherein the retinal degeneration occurs in age-related macular degeneration (AMD).

These and other aspects will be readily apparent to the skilled artisan in light of disclosure as a whole.

BRIEF DESCRIPTION OF THE DRAWINGS

FIG. 4B shows a section from an eye of a rat treated, at 4 weeks after birth, by intravitreal injection of $1.5 \times 10^5$ SB623 cells. FIG. 4A shows a section from an eye of a control rat into which PBS was injected at 4 weeks after birth. A well-developed outer nuclear layer (indicated the figure) is present in the SB623-treated eyes, but absent in vehicle-treated eyes.

FIGS. 5A and 5C show H&E- stained sections; FIGS. 5B and 5D show sections stained with anti-human mitochondria antibody (green) and counterstained with the nucleus-specific dye DAN (blue). The two upper panels show a section containing a clump of SB623 cells in the vitreous body. The two lower panels show a section of retina in which a SB623 cell can be seen on the inner limiting membrane of the retina.

FIG. 10, panels A and B, shows hematoxylin and eosin (H&E)-stained sections of RCS rat retina at 27 weeks after treatment. FIG. 10B shows a section from an eye of a rat treated, at 4 weeks after birth, by subretinal injection of $1.5 \times 10^5$ SB623 cells. FIG. 10A shows a section from an eye of a control rat into which PBS was injected at: 4 weeks after birth. A well-developed outer nuclear layer (indicated "ONL" in the figure) is present in the SB623-treated eyes, but absent in vehicle-treated eyes.

FIG. 11, panels A and B, shows sections of retina from RCS rats 27 weeks after subretinal injection of $1.5 \times 10^5$ SB623 cells (31 weeks postnatal). FIG. 11A shows a EWE-stained section: FIG. 11B shows a section stained with anti-human mitochondria antibody (green) and counterstained with the nucleus-specific dye DAPI (blue). Transplanted SB623 cells are visible in the FIG. 11A (arrowheads).

DETAILED DESCRIPTION

Figure 1:
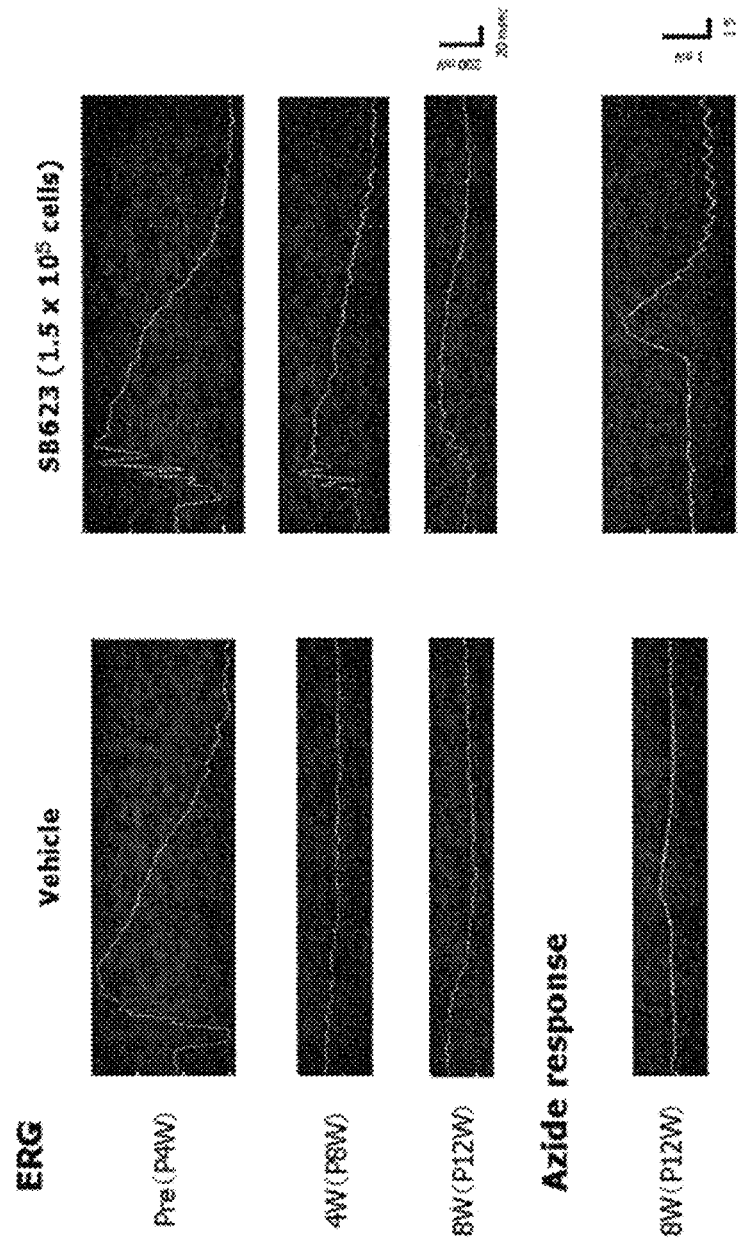
FIG. 1 shows representative electroretinogram (ERG) traces from the eyes of RCS rats at 4 weeks after birth (prior to treatment, top set of panels), 8 weeks after birth (4 weeks after treatment, second set of panels from top) and 12 weeks after birth (8 weeks after treatment, third set of panels from top). Rats were treated at 4 weeks after birth by intravitreal injection of either $1.5 \times 10^5$ SB623 cells (right panels) or PBS (left panels). The bottom set of panels shows photoreceptor activity as assayed by azide responses at 12 weeks after birth (8 weeks after treatment) for rats that were treated at 4 weeks after birth by intravitreal injection of either $1.5 \times 10^5$ SB623 cells (right panel) or PBS (left panel).

Disclosed herein are methods and compositions for the treatment of retinal degeneration and retinal degenerative conditions. In particular, transplantation of SB623 cells (cells obtained by transfecting mesenchymal stem cells with sequences encoding a. Notch intracellular domain) into the eyes of subjects undergoing retinal degeneration (or suffering from a retinal degenerative condition) prevents retinal degeneration and results in long-term rescue of retinal function.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. el al., "Molecular Biology of the Cell," $5^{th}$ edition, Garland Science, New York, N.Y., 2008; Voet, D et al. "Fundamentals of Biochemistry; Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. el al., "Current Protocols in Molecular Biology," John Wiley & Sons, New York, 1987 and periodic updates; Freshney, R. I., "Culture of Animal Cells: A Manual of Basic Technique," $4^{th}$ edition, John Wiley & Sons, Somerset, N.J., 2000; and the series "Methods in Enzymology," Academic Press, San Diego, Calif.

Retinal Degeneration

Two of the most commonly-occurring retinal degenerative conditions are retinitis pigmentosa (RP) and age-related macular degeneration (AMD). Retinitis pigmentosa results from degeneration of the photoreceptor cells of the retina, also known as rods and cones. The macula is the name given to the central portion of the retina and is responsible for central, as opposed to peripheral, vision. There are two forms of AMD. The more common form, dry AMD, is caused by the buildup of cellular debris (drusen) between the retina and the choroid (the layer of the eye beneath the retina), leading to atrophy of photoreceptor cells. The other form of AMD, wet AMD, results from abnormal growth of blood vessels in the choroid. These vessels may leak, resulting in damage to the choroid and the retina. Other terms for AMD include choroidal neovascularization, subretinal neovascularization, exudative form and disciform degeneration.

Other types of retinal degenerative conditions include Usher syndrome (an inherited condition characterized by hearing loss and progressive loss of vision from RP), Stargardt's disease (inherited juvenile macular degeneration), Leber Congenital Amaurosis (an inherited disease characterized by loss of vision at birth), choroideremia (an inherited condition causing progressive vision loss due to degeneration of the choroid and retina), Bardet-Biedl syndrome (a complex of disorders that includes retinal degeneration and can also include polydactyly and renal disease), and Refsum disease (a disorder caused by inability to metabolize phytanic acid which is characterized by, inter alia, RP). See, ex., Goodwin (2008) Curr Opin Ophthalmol 19(3):255-62; Bonnet et al, (2012) Curr Opin Neurol. 25(1):42-9; Coussa et al. (2012) Ophthalmic Genet. 33(2):57-65.

Other, rarer retinal degenerative conditions that can be treated using the methods and compositions described herein include Best's disease, cone-rod retinal dystrophy, gyrate atrophy. Oguchi disease, juvenile retinoschisis, Bassen-Kornzweig disease (abetalipoproteinemia), blue cone monochromatism disease, dominant drusen, Goldman-Favre vitreoretinal dystrophy (enhanced S-cone syndrome), Kearns-Sayre syndrome, Laurence-Moon syndrome, peripapillary choroidal dystrophy, pigment pattern dystrophy, (including Butterfly-shaped pigment dystrophy of the fovea, North Carolina macular dystrophy, macro-reticular dystrophy, spider dystrophy and Sjogren reticular pigment epithelium dystrophy), Sorsby macular dystrophy, Stickler's syndrome and Wagner's syndrome vitreoretinal dystrophy).

SB623 Cells

The present disclosure provides methods for treating retinal degeneration by transplanting SB623 cells into the eye of a subject in need thereof namely a subject in which retinal degeneration is occurring. SB623 cells are obtained from marrow adherent stromal cells (MASCs), also known as mesenchymal stem cells (MSCs), by expressing the intracellular domain of the Notch protein in the MASCs. MASC's are obtained by selecting adherent cells from bone marrow.

In one embodiment, a culture of MASCs is contacted with a polynucleotide comprising sequences encoding a NICD (e.g., by transfection), followed by enrichment of transfected cells by drug selection and further culture. See, for example, U.S. Pat. No. 7,682,825 (issued Mar. 23, 2010); U.S. Patent Application Publication No. 2010/0266554 (Oct. 21, 2010); and WO 2009/023251 (Feb. 19, 2009); all of which disclosures are incorporated by reference, in their entireties, for the purposes of describing isolation of mesenchymal stem cells and conversion of mesenchymal stem cells to SB623 cells (denoted "neural precursor cells" and "neural regenerating cells" in those documents). See also Example 1, infra.

In these methods, any polynucleotide encoding a Notch intracellular domain (e.g., vector) can be used, and any method for the selection and enrichment of transfected cells can be used. For example, in certain embodiments, MASCs are transfected with a vector containing sequences encoding a Notch intracellular domain and also containing sequences encoding a drug resistance marker (e.g. resistance to G418). In additional embodiments, two vectors, one containing sequences encoding a Notch intracellular domain and the other containing sequences encoding a drug resistance marker, are used for transfection of MASCs. In these embodiments, selection is achieved, after transfection of a cell culture with the vector or vectors, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector. Following selection (e.g., for seven days) the selective agent is removed and the cells are further cultured (e.g., for two passages).

Preparation of SB623 cells thus involves transient expression of an exogenous Notch intracellular domain in a MSC. To this end, MSCs can be transfected with a vector comprising sequences encoding a Notch intracellular domain wherein said sequences do not encode a full-length Notch protein. All such sequences are well known and readily available to those of skill in the art. For example, Del Amo et al. (1993) *Genomics* 15:259-264 present the complete amino acid sequences of the mouse Notch protein; while Mumm and Kopan (2000) *Devel. Biol.* 228:151-165 provide the amino acid sequence, from mouse Notch protein, surrounding the so-called S3 cleavage site which releases the intracellular domain. Taken together, these references provide the skilled artisan with each and every peptide containing a Notch intracellular domain that is not the full-length Notch protein; thereby also providing the skilled artisan with every polynucleotide comprising sequences encoding a Notch intracellular domain that does not encode a full-length Notch protein. The foregoing documents (Del Amo and Mumm) are incorporated by reference in their entireties for the purpose of disclosing the amino acid sequence of the full-length Notch protein and the amino acid sequence of the Notch intracellular domain, respectively.

Similar information is available for Notch proteins and nucleic acids from additional species, including rat, *Xenopus, Drosophila* and human. See, for example, Weimnaster et al. (1991) *Development* 113:199-205; Schroeter et al. (1998) *Nature* 393:382-386; NCB1 Reference Sequence No NM_017167 (and references cited therein); SwissProt P46531 (and references cited therein); SwissProt Q01705 (and references cited therein); and GenBank CA840733 (and references cited therein). The foregoing references are incorporated by reference in their entireties for the purposes of disclosing the amino acid sequence of the full-length Notch protein and the amino acid sequence of the Notch intracellular domain in a number of different species.

In additional embodiments, SB623 cells are prepared by introducing, into MSCs, a nucleic acid comprising sequences encoding a Notch intracellular domain such that the MSCs do not express exogenous Notch extracellular domain. Such can be accomplished, for example, by transfecting MSCs with a vector comprising sequences encoding a Notch intracellular domain wherein said sequences do not encode a full-length Notch protein.

Additional details on the preparation of SB623 cells, and methods for making cells with properties similar to those of SB623 cells which can be used in the methods disclosed herein, are found in U.S. Pat. No. 7,682,825; and U.S. Patent Application Publication Nos. 2010/0266554 and 2011/0229442: the disclosures of which are incorporated by reference herein for the purposes of providing additional details on the preparation of SB623 cells, and for providing methods for making cells with properties similar to those of SB623 cells. See also Dezawa et al. (2004) *J. Clin. Invest.* 113:1701-1710.

Formulations, Kits and Routes of Administration

Therapeutic compositions comprising SB623 cells as disclosed herein are also provided. Such compositions typically comprise the SB623 cells and a pharmaceutically acceptable carrier.

The therapeutic compositions disclosed herein are useful for inter alia, reducing the progress of retinal degeneration, reversing retinal degeneration and/or restoring photoreceptor function. Accordingly, a "therapeutically effective amount" of a composition comprising SB623 cells can be any amount that prevents or reverses retinal degeneration and/or restores photoreceptor function. For example, dosage amounts can vary from about 100; 500; 1,000; 2,500; 5,000; 10,000; 20,000; 50,000; 100,000; 500,000; 1,000,000; 5,000,000 to 10,000,000 cells or more (or any integral value therebetween); with a frequency of administration of e.g., once per day, twice per week, once per week, twice per month, once per month, depending upon, e.g., body weight, route of administration, severity of disease, etc.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The cells described herein can be suspended in a physiologically compatible carrier for transplantation. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential medium), phosphate buffered saline, Hank's balanced salt solution+/−glucose (HBSS), and multiple electrolyte solutions such as Plasma-Lyte™ A (Baxter).

The volume of a SB623 cell suspension administered to a subject will vary depending on the site of transplantation, treatment goal and number of cells in solution. Typically the amount of cells administered will be a therapeutically effective amount. As used herein, a "therapeutically effective amount" or "effective amount" refers to the number of transplanted cells which are required to effect treatment of the particular disorder; i.e., to produce a reduction in the amount and/or severity of the symptoms associated with that disorder. For example, in the case of treatment for AMD, transplantation of a therapeutically effective amount of SB623 cells typically results in prevention or reversal of retinal degeneration and/or restoration of photoreceptor function. Therapeutically effective amounts vary with the type and extent of retinal degeneration, and can also vary depending on the overall condition of the subject.

The disclosed therapeutic compositions can also include pharmaceutically acceptable materials, compositions or vehicle, such as a liquid or solid filler, diluent, excipient, solvent or encapsulating material, i.e., carriers. These carriers can, for example, stabilize the SB623 cells and/or facilitate the survival of the SB623 cells in the body. Each carrier should be "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Exemplary formulations include, but are not limited to, those suitable for parenteral administration, e.g., intrapulmonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non systemically, thereby reducing the body burden of the composition as compared to systemic delivery. Such local delivery can be achieved, for example, through the use of various medically implanted devices including, but not limited to, stems and catheters, or can be achieved by inhalation, phlebotomy, injection or surgery. Methods for coating, implanting, embedding, and otherwise attaching desired agents to medical devices such as stems and catheters are established in the art and contemplated herein. Local delivery can also be achieved, for example, by intra-ocular injection or by application of eye drops.

Another aspect of the present disclosure relates to kits for carrying out the administration of SB623 cells to a subject. In one embodiment, a kit comprises a composition of SB623 cells, formulated as appropriate (e.g., in a pharmaceutical carrier), in one or more separate pharmaceutical preparations.

Administration

For treatment of retinal degeneration (e.g., AMD) with SB623 cells, any method known in the art for delivery of substances to the eye can be utilized. For the purposes of this disclosure, "transplantation" refers to the transfer of SB623 cells to the eye of a subject, by any method. For example, direct injection into the eye can be used for delivery of a suspension of SB623 cells. In certain embodiments, a suspension of SB623 cells is injected into the vitreous humor. In other embodiments, subretinal injection is used. In additional embodiments, topical administration is used for example, therapeutic compositions can be formulated in a solution to be used as eye drops. In still other embodiments, topical application of suspensions, gels and the like can utilized for administration of SB623 cells.

EXAMPLES

Proper function of photoreceptor cells involves continual synthesis and shedding of photoreceptor outer segments. Cells of the retinal pigmented epithelium (RPE cells) aid in this process by phagocytosing shed outer segments, and by recycling retinoids and membrane lipids.

The Royal College of Surgeons rat ("RCS rat") is an animal model of inherited retinal degeneration, in which retinal degeneration results from defective RPE cells that are unable to phagocytose photoreceptor outer segments. D'Cruz t al. (2000) *Human Molecular Genetics* 9(4):645-651. Histologically, the retina of the RCS rat is characterized by abnormal accumulation of outer segment debris between the photoreceptor cell outer segment layer and the retinal pigmented epithelium. Accumulation occurs prior to, and concomitant with, the death of photoreceptor cells. RCS rats experience progressive postnatal loss of photoreceptor cells and attendant loss of vision.

Electroretinography is a process in which an electrode is placed on the cornea, the eye is stimulated by a flash of light, and the electrical activity of photoreceptor cells is measured by the electrode. Odom S V, Leys M, Weinstein G W. Clinical visual electrophysiology. In: Tasman W. Jaeger E A, eds, *Duane's Ophthalmology*, 15th ed. Philadelphia., Pa.: Lippincott Williams & Wilkins; 2009: chap 5; Baloh R W, Jen J. Neuro-ophthalmology. In: Goldman L, Schafer A I, eds. *Cecil Medicine*. 24th ed. Philadelphia, Pa.: Saunders Elsevier; 2011: chap 432; Cleary T S, Reichel E. Electrophysiology. In: Yanoff M, Duker J S, eds. *Ophthalmology*. 3rd ed. St. Louis, Mo.: Mosby Elsevier; 2008: chap 6.9.

Another measure of photoreceptor function that can be measured by retinography is a peak of electrical activity between 0.05 and 50 Hz following systemic introduction of sodium azide, known as the azide response.

Example 1

Preparation of SB623 Cell Suspensions

SB623 cells were obtained by transfection of human marrow adherent stem cells (MASCs) with DNA encoding the intracellular domain of the human Notch protein. MASCs were obtained from human bone marrow as follows. Human adult bone marrow aspirates were purchased from Lonza (Walkersville, Md.). Cells were washed once, and plated in Corning T225 flasks (Corning, Inc Lowell, Mass.) in Growth Medium: alpha-MEM (Mediatech, Herndon, Va.) supplemented with 10% fetal bovine serum (FBS) (Hyclone, Logan. Utah), 2 mM L-glutamine and penicillin/streptomycin (both from Invitrogen, Carlsbad, Calif.). After 3 days, unattached cells were removed; and the MASC cultures were maintained, in growth medium for approximately 2 weeks. During that period, cells were passaged twice, using 0.25% Trypsin/EDTA To make SB623 cells, the MASCs were transfected with the pN-2 plasmid, which contains sequences encoding the human Notch1 intracellular domain (under the transcriptional control of the CMV promoter) and a neomycin-resistance gene (under the transcriptional control of a SV40 promoter), using Fugene6 (Roche Diagnostics, Indianapolis, Ind.) according to the manufacturer's instructions. Briefly, cells were incubated with the Fugene6/plasmid DNA complex for 24 hours. The next day, medium was replaced with growth medium (components described above) containing 100 ug/ml G418 (Invitrogen, Carlsbad, Calif.), and selection was continued for 7 days. After removal of G418 selection medium, cultures were maintained in growth medium and expanded for 2 passages. SB623 cells were harvested using Trypsin/EDTA, formulated in freezing medium at cell densities of $7.5 \times 10^3$, $1.5 \times 10^4$ and $3 \times 10^4$ cells/ml and cryopreserved. Frozen SB623 cells were stored in the vapor phase of a liquid $N_2$ unit until needed.

Example 2

Intravitreal Transplantation

RCS rats were immunosuppressed by administration of oral cyclosporine A (200 mg/l in drinking water) beginning at postnatal day 2 and continuing until transplantation. Transplantation of SB623 cells by injection occurred at four weeks after birth. Prior to transplantation, animals were systemically anesthetized with a mixture of xylazine hydrochloride (Celactal®, Bayer Medical, Ltd.) and ketamine hydrochloride (Ketalar®, Daiichi Sankyo Co. Ltd.) and topically anesthetized with 0.4% oxybpurocaine hydrochloride (Benoxyl®, Santen Pharmaceutical Co., Ltd.). Pupils were dilated with tropicamide and phenylephrine hydrochloride (Mydrin-P®, Santen Pharmaceutical Co., Ltd.) prior to injection of 5 ul of SB623 cell suspension into the vitreous cavity. Injection was accomplished using a Hamilton syringe with a 30-gauge needle. Control cohorts were injected with vehicle (PBS) or were uninfected (naïve). The experimental design is shown in Table 1.

TABLE 1

| Group | Treatment | Cell number (per eye) | Number of animals |
|---|---|---|---|
| 1 | Naïve | — | 5 |
| 2 | Vehicle (PBS) | — | 5 |
| 3 | SB623 | $3.75 \times 10^4$ | 5 |
| 4 | SB623 | $7.5 \times 10^4$ | 5 |
| 5 | SB623 | $1.5 \times 10^5$ | 7 |

Following transplantation of SB623 cells at 4 weeks of age, animals were tested at 5, 6, 8 and 12 weeks of age (i.e., 1, 2, 4 and 8 weeks after transplantation) by electroretinography and at 12 weeks of age (S weeks post-transplantation) for azide response. At 13 weeks of age (9 weeks after treatment), animals were sacrificed, and their eyes were removed for histological examination.

For electroretinography, rats were dark-adapted for one hour, then systemically anesthetized with a mixture of xylazine hydrochloride (Celactal®, Bayer Medical, Ltd.) and ketamine hydrochloride (Ketalar®, Daiichi Sankyo Co., Ltd.). Pupils were dilated with tropicamide and phenylephrine hydrochloride (Mydrin-P®, Santen Pharmaceutical Co., Ltd.). Electroretinograms (ERGs) were recorded with a contact electrode placed on the cornea and a grounding electrode placed in the nose. Responses were evoked with a white LED flash ($3,162$ cd/m$^2$, 10 ms duration) and recorded on a Neuropack S1 NEB9404 (Nihon Kohden Corp.).

Figure 2:
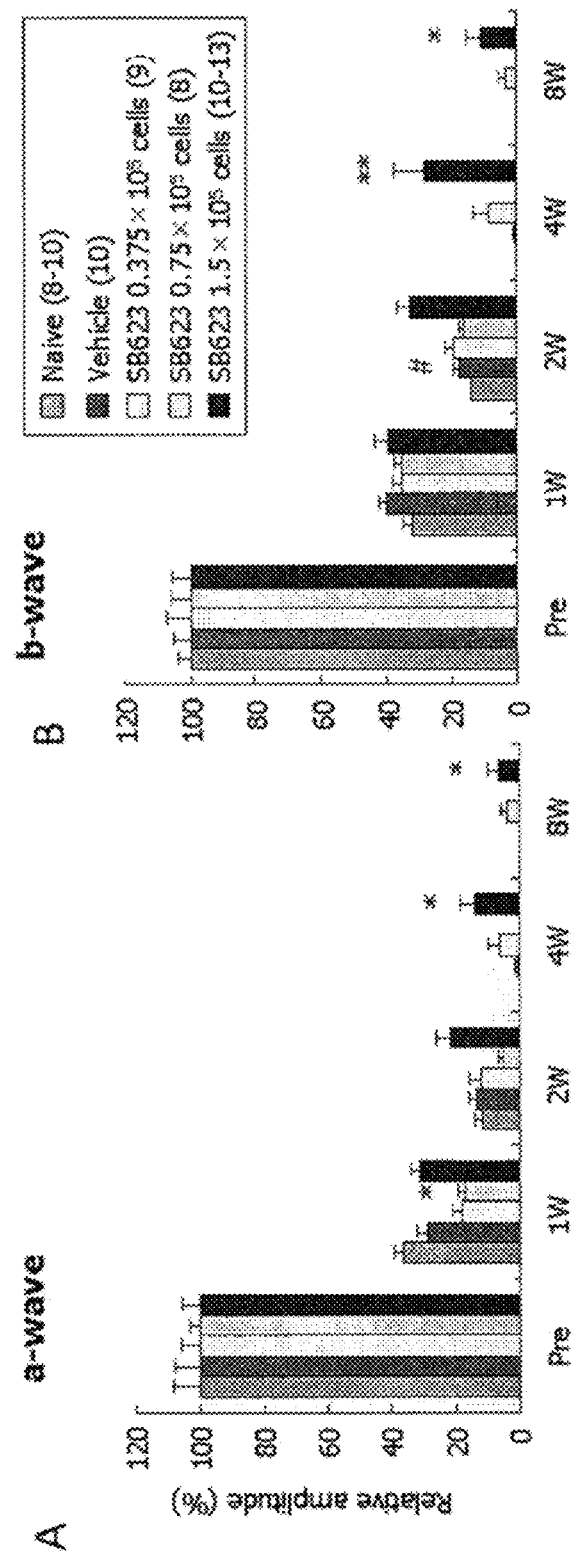
FIG. 2, panels A and B, shows a set of graphs depicting relative amplitudes of a-waves (FIG. 2A) and b-waves (FIG. 2B) from electroretinograms of RCS rats taken at 4, 5, 6, 8 and 12 weeks after birth (i.e., pre-treatment and at 1, 2, 4 and 8 weeks after treatment). For each set of bars, the left-most bar represents the value for naïve (i.e. untreated) animals. Proceeding rightward, the remaining bars represent values for animals treated by intravitreal injection of vehicle, $0.375 \times 10^5$ SB623 cells. $0.75 \times 10^5$ SB623 cells and $1.5 \times 10^5$ SB623 cells. Numbers in parentheses indicate the number of eyes analyzed. Pretreatment values were set as 100%.

FIG. 1 (upper three pairs of panels) shows representative ERG traces, for vehicle-treated animals (left panels) and for animals treated with $1.5 \times 10^5$ SB623 cells per eye (right panels), obtained just prior to transplantation (at 4 weeks after birth), and at 4 and 8 weeks post-transplantation. Neither an a-wave nor a b-wave was observed in the vehicle-treated animals at 4- and 8-weeks post-treatment; while, in the SB623-treated animals, electrical activity was retained at these time points. A quantitative assessment of receptor cell electrical activity, measured by ERG, is shown in FIG. 2. At all time points tested, SB623-treated animals retained greater photoreceptor cell electrical activity that either naïve animals or vehicle-treated animals.

For determination of azide responses at 8 weeks post-transplantation, RCS rats were dark-adapted for one hour, then systemically anesthetized with a mixture of xylazine hydrocholride (Celactal®, Bayer Medical, Ltd.) and ketamine hydrochloride (Ketalar®, Daiichi Sankyo Co., Ltd.) and topically anesthetized with 0.4% oxybupurocaine hydrochloride (Benoxyl®, Santen Pharmaceutical Co., Ltd.). A contact electrode was placed on the cornea, and 0.1 ml of 0.1% sodium azide (NaN) was injected into the caudal vein. Responses were recorded on a Neuropack S1 NEB9404 (Nihon Kohden Corp.), amplified in the region between 0.05 and 50 Hz. Amplitudes were measured from baseline to the positive peak, which appeared approximately 4 seconds after injection of the azide solution.

Figure 3:
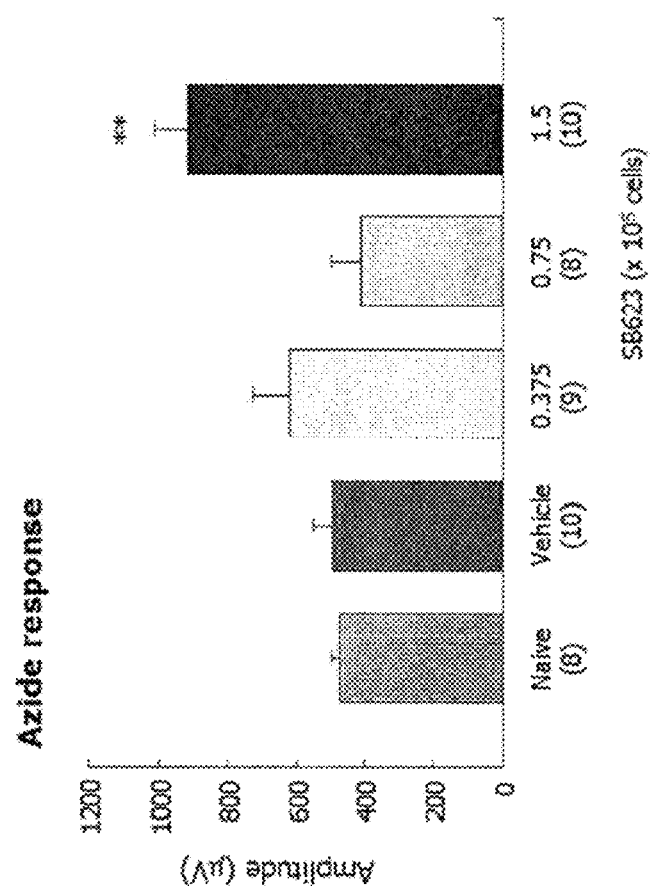
FIG. 3 is a graph showing amplitudes (in microvolts) of the azide response in eyes of RCS rats at 12 weeks after birth (8 weeks after treatment). Animals were untreated ("Naïve") or subjected to intravitreal injection, at 4 weeks of age, with PBS ("Vehicle"), $0.375 \times 10^5$ SB623 cells, $0.75 \times 10^5$ SB623 cells, or $1.5 \times 10^5$ SB623 cells. Numbers in parentheses indicate the number of eyes analyzed.

The lower pair of panels in FIG. 1 shows that the azide response was retained, at 8 weeks after treatment, in the eyes of RCS rats treated by intravitreal injection of $1.5 \times 10^5$ SB623 cells (lower right panel) but was lost in rats injected with PBS (lower left panel). FIG. 3 shows measurements of the amplitude of the response in SB623-treated and control eyes. As shown, injection of $1.5 \times 10^5$ SB623 cells resulted in a statistically significant increase in the amplitude of the azide response at 8 weeks after treatment.

For histological analysis, rats were sacrificed, and their eyes were removed. After fixation in 4% paraformaldehyde, eyes were embedded in Technovit® 8100 resin (Heraeus Kulzer, Werheim, Germany) according to the manufacturer's instructions. Briefly, eyes were washed overnight at 4° C. in PBS containing 6.8% sucrose, dehydrated in 100% acetone, and embedded in Cryomold® (EMS, Hatfield, Pa.). The polymerized block was fixed onto a wooden block with an adhesive agent and cut using as sliding microtome (HM440E, MICROM International GmbH, Walldorf, Germany) with a disposable knife. Three-micrometer sections were used for immunostaining with a human anti-mitochondrial antibody (Millipore MAB1273).

Figure 4:
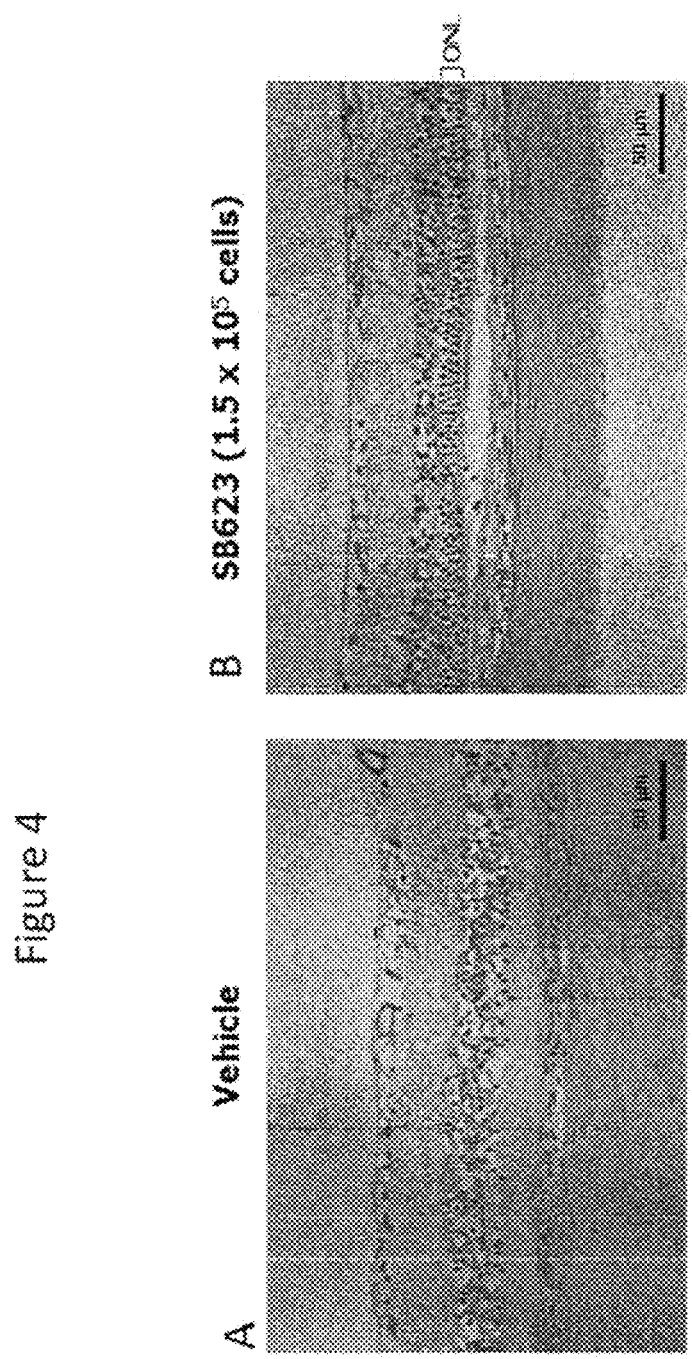
FIG. 4, panels A and B, shows hematoxylin and eosin (H&E)-stained sections of RCS rat retina at 9 weeks after treatment.
Figure 5:
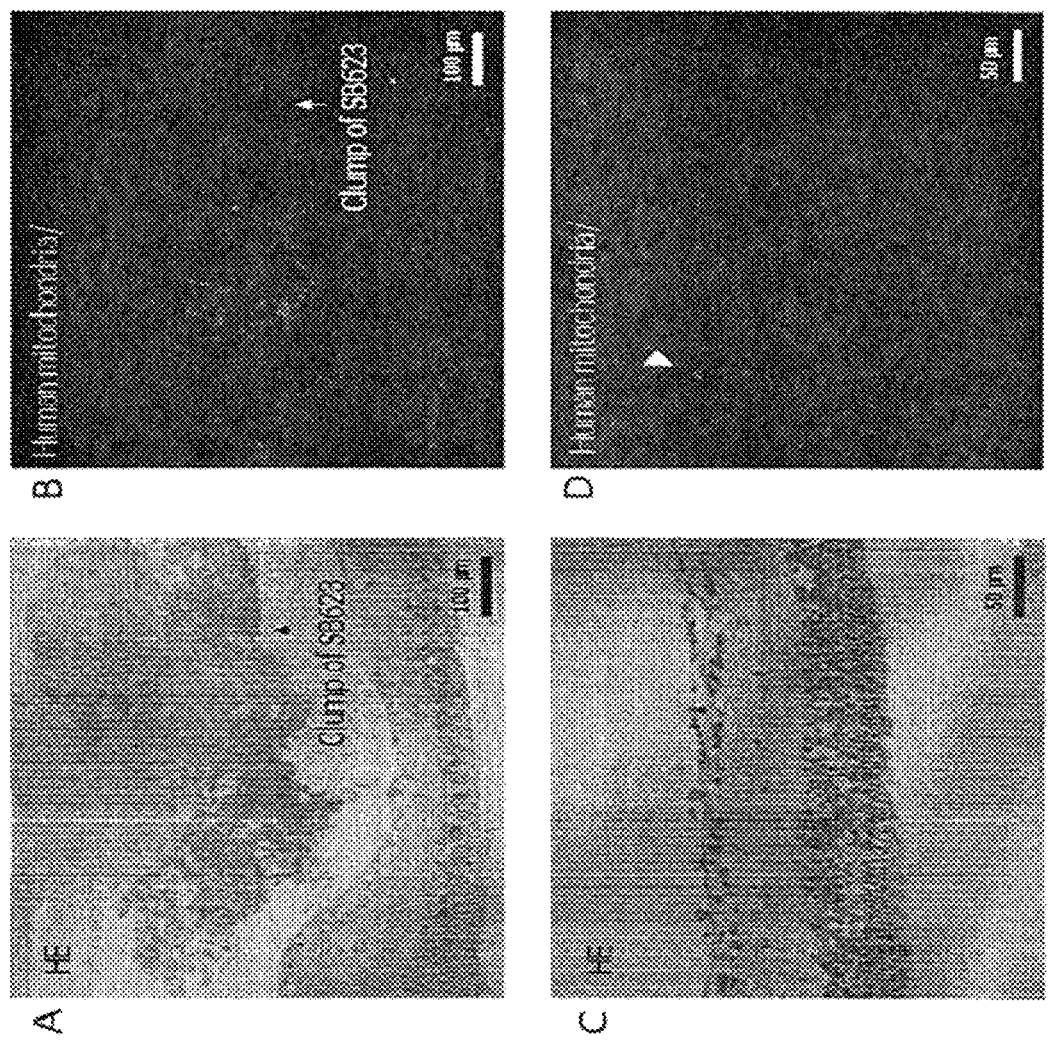
FIG. 5, panels A to D, shows sections of retinas from RCS rats nine weeks after intravitreal injection of $1.5 \times 10^5$ SB623 cells (13 weeks postnatal).

Histological analysis revealed that, in vehicle-treated eyes, most of the cells of the outer nuclear layer of the retina were absent by 9 weeks after treatment (FIG. 4A). In contrast, in SB623-treated eyes, cells of the outer nuclear layer were well-preserved (FIG. 4B). Clumps of transplanted SB623 cells were observed in the vitreous body (FIGS. 5A and 5B) and a SB623 cell was also observed on the inner limiting membrane of the retina (FIGS. 5C and 5E)). In additional experiments, it was observed that intravitreal transplantation of SB623 cells prevented loss of outer nuclear layer cells for up to 25 weeks after treatment, and that SB623 cells persisted in the vitreous body at this time.

The results of both electrophysiological and morphological analyses, presented above, indicate that intravitreal transplantation of SB623 cells preserved retinal function.

Example 3

Subretinal Transplantation

SB623 cells were prepared as described in Example 1 and suspended in PBS to a density of $3 \times 10^4$ cells/ul. Immunosuppression of RCS rats, systemic and topical anesthesia, and dilation of pupils were all conducted as described in Example 2. Transplantation of SB623 cells occurred at four weeks after birth, by injection of 5 ul of SB623 cell suspension intravitreously into the subretinal space using a Hamilton syringe with a 30-gauge needle. Control cohorts were injected with vehicle (PBS) or were uninjected (naïve). The experimental design is shown in Table 2. In this experiment, analysis was continued for a longer period after treatment: electroretinography and azide response measurements were continued for 24 weeks, and histology and immunohistochemistry were conducted on specimens obtained 27 weeks after treatment.

TABLE 2

| Group | Treatment | Cell number (per eye) | Number of animals |
|---|---|---|---|
| 1 | Naive | — | 4 |
| 2 | Vehicle (PBS) | — | 10 |
| 3 | SB623 | $1.5 \times 10^5$ | 10 |

Figure 6:
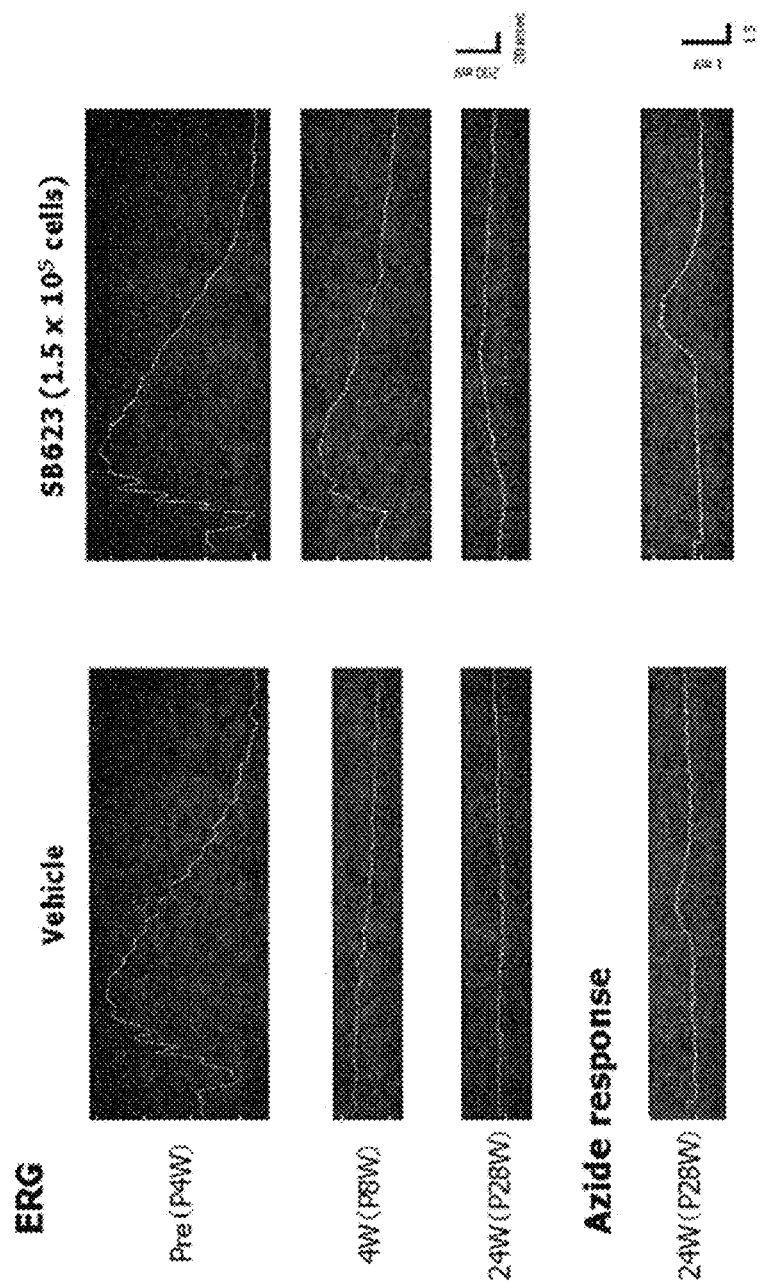
FIG. 6 shows representative electroretinogram (ERG) traces from the eyes of RCS rats at 4 weeks after birth (prior to treatment, top set of panels), 8 weeks after birth (4 weeks after treatment, second set of panels from top) and 28 weeks after birth (24 weeks after treatment, third set of panels from top). Rats were treated at 4 weeks after birth by subretinal injection of either $1.5 \times 10^5$ SB623 cells (right panels) or PBS (left panels). The bottom set of panels shows photoreceptor activity as measured by azide responses at 28 weeks after birth (24 weeks after treatment) for rats that were treated at 4 weeks after birth by subretinal injection of either $1.5 \times 10^5$ SB623 cells (right panel) or PBS (left panel).

Electroretinography and determination of azide responses were conducted as described in Example 2, Representative results are shown in FIG. 6. In most vehicle-treated rats, an ERG could not be recorded at 4 weeks after treatment (FIG. 6, left panels). However, in SB623-treated animals, both ERGs and azide responses were retained at 24 weeks after treatment (FIG. 6, right panels).

Figure 7:
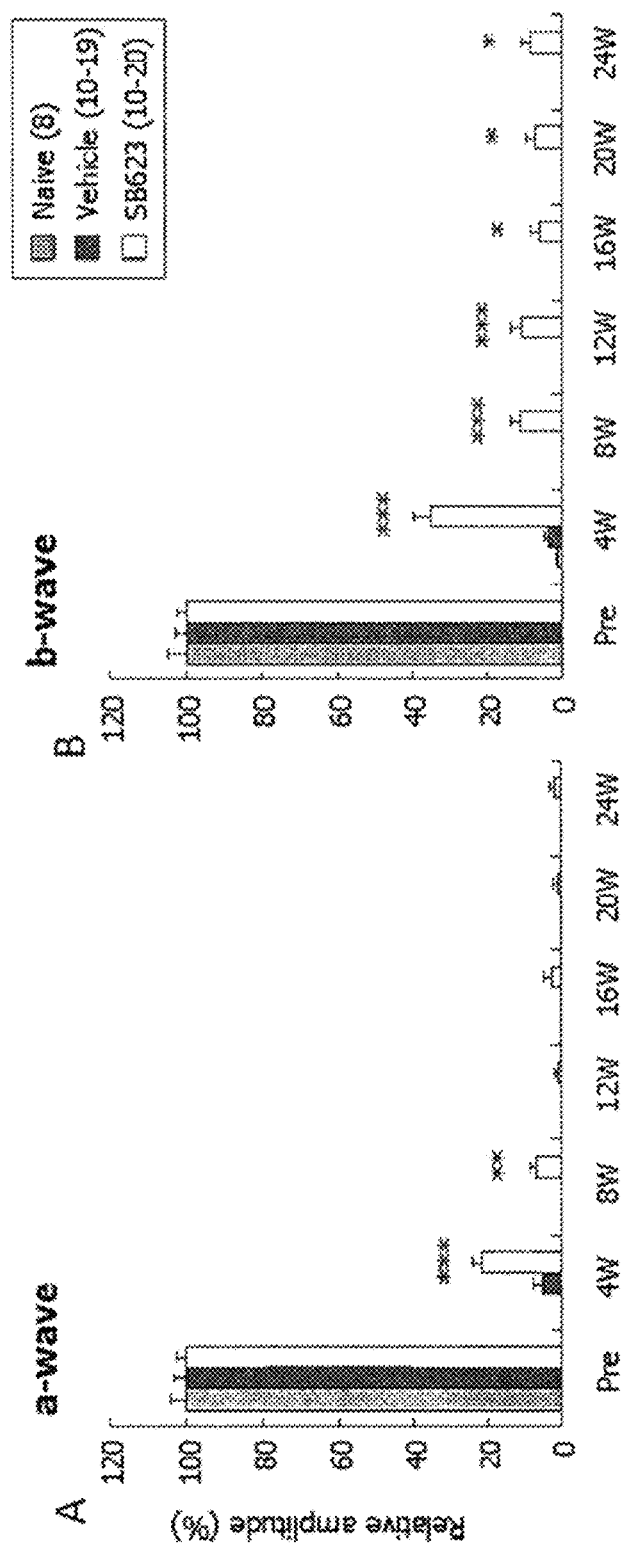
FIG. 7, panels A and B, shows a set of graphs depicting relative amplitudes of a-waves (FIG. 7A) and b-waves (FIG. 7B) from electroretinograms of RCS rats taken pre-treatment and at 4, 8, 12, 16, 20 and 24 weeks after treatment. For each set of bars, the left-most bar represents the value for naïve untreated) animals; the middle bar represents values for animals treated by subretinal injection of vehicle; and the right-most bar represents values for animals treated by subretinal injection of $1.5 \times 10^5$ SB623 cells. Numbers in parentheses indicate the number of eyes analyzed. Pretreatment amplitude was set as 100%.

FIG. 7 shows a time-course of changes in ERG amplitudes at four-week intervals up to 24 weeks post-transplantation. By 8 weeks after transplantation, neither an a-wave nor a b-wave could be detected in eyes from naïve and vehicle-treated rats; but in rats that had received a subretinal injection of SB623 cells, both a- and b-waves were retained up to 24 weeks post-treatment.

Figure 8:
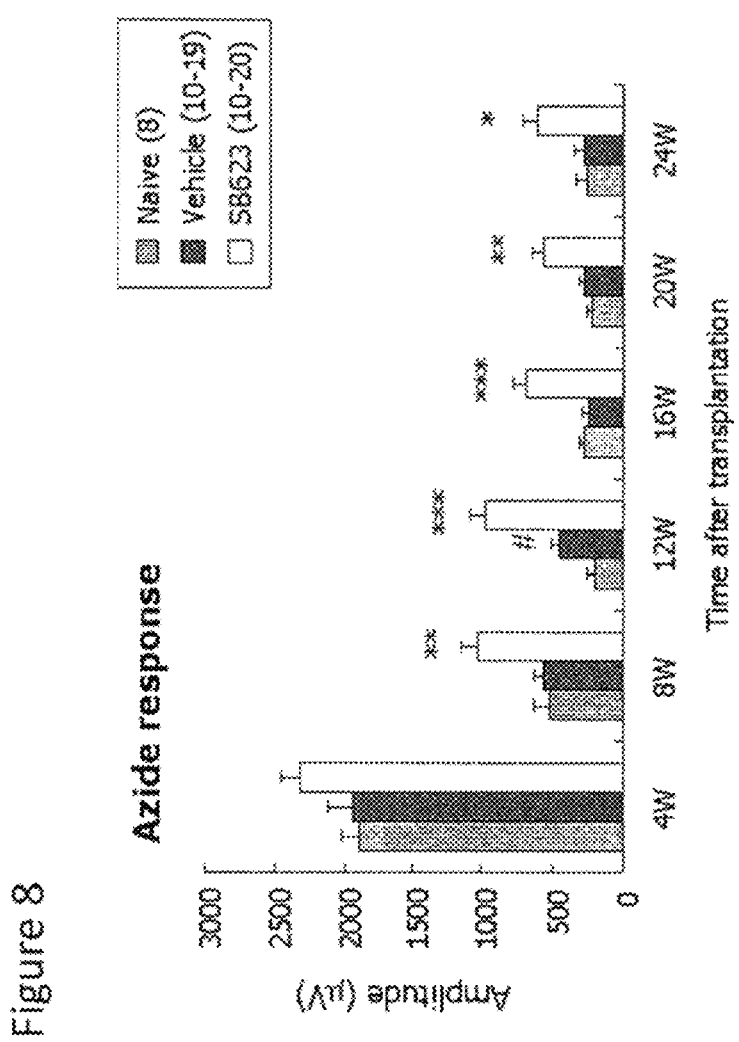
FIG. 8 is a graph showing amplitudes (in microvolts) of the azide response in eyes of RCS rats at 4, 8, 12, 16, 20 and 24 weeks after treatment. For each set of three bars, the left-most bar represents the value for naïve (Le, untreated) animals; the middle bar represents values for animals treated by subretinal injection of vehicle; and the right-most bar represents values for animals treated by subretinal injection of $1.5 \times 10^5$ SB623 cells. Numbers in parentheses indicate the number of eyes analyzed.

FIG. 8 shows a time-course of changes in the azide response at four-week intervals up to 24 weeks post-transplantation. The response is reduced in naïve and vehicle-injected animals at all time points. In rats that had received a subretinal injection of SB623 cells, a statistically significant increase in azide response, compared to naïve and vehicle-injected rats was observed at all points up to 24 weeks post-treatment.

The results of these electrophysiological examinations indicate that transplantation of SB623 cells preserves retinal function for long-term periods.

Figure 9:
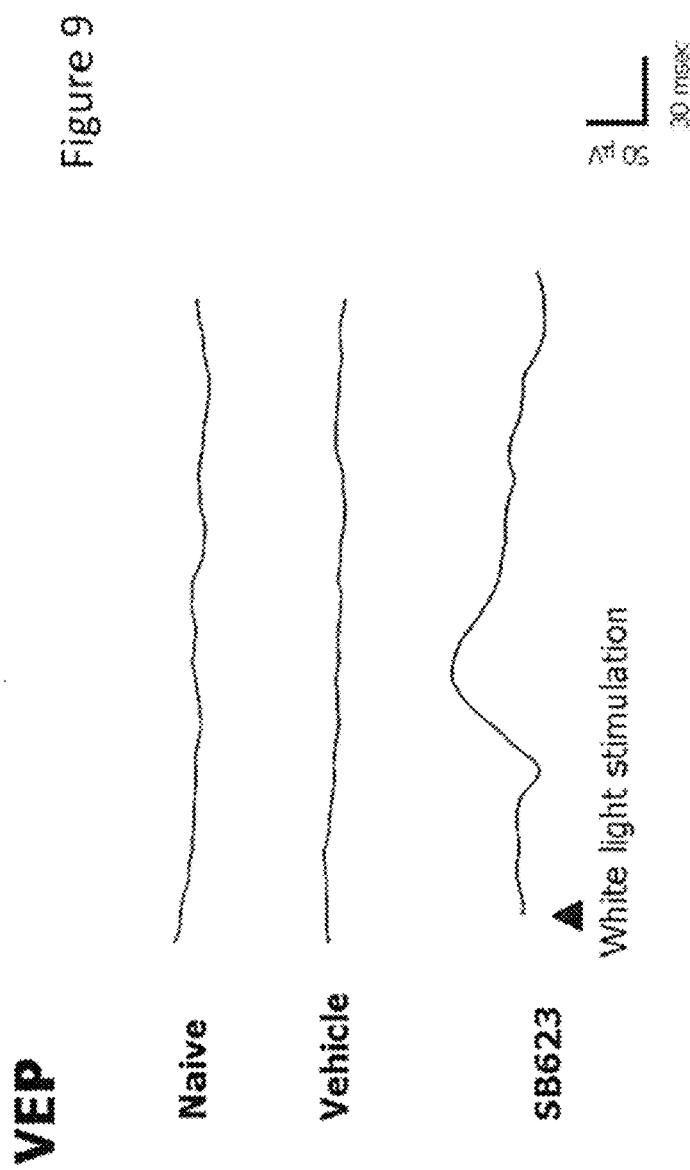
FIG. 9 shows traces of visually evoked potential (VEP), taken 26 weeks after subretinal transplantation, from naïve, vehicle-treated and SB623 cell-treated RCS rats.

To determine whether visual signals were transmitted from the retina to the visual cortex of the brain, visually evoked potentials (VEPs) were measured, in treated and untreated RCS rats, at 26 weeks after treatment. Seven days prior to VEP recording, screw electrodes were placed epidurally on each side of the head 6.8 mm behind the bregma and 3.2 mm lateral of the midline, and a reference electrode was placed epidurally on the midline 11.8 mm behind the bregma. On the day of VEP recording, rats were dark-adapted for one hour, then systemically anesthetized with a mixture of xylazine hydrochloride (Celactal®, Bayer Medical, Ltd,) and ketamine hydrochloride (Ketalar®, Daiichi Sankyo Co., Ltd.). Pupils were dilated with tropicamide and phenylephrine hydrochloride (Mydrin-P®, Santen Pharmaceutical Co., Ltd.). VEP responses were evoked with a white LED flash ($3,162$ cd/m$^2$, 10 ms duration) and recorded on a Neuropack S1 NEB9404 (Nihon Kohden Corp.). One hundred responses were measured and the results were averaged. Representative results are shown in FIG. 9. In naïve and vehicle-injected animals, VEPs could not be detected. In contrast, the VEP response was well-preserved, at 26 weeks after treatment, in rats that had been subretinally injected with SB623 cells. These results indicate that treatment with SB623 cells restores the ability to send visual signals to the visual cortex.

Histology and immunochemistry were conducted, as described in Example 2, on specimens obtained 27 weeks after treatment. As shown in FIG. 10, by 27 weeks after transplantation, few if any cells of the outer nuclear layer (ONL) were present in vehicle-treated rats. However, in SB623-treated rats, cells of the ONI, were well-preserved at 27 weeks. in addition, transplanted SB623 cells, detected by immunostaining with anti-human mitochondrial antibody, were observed in the subretinal space (FIG. 11).

These results demonstrate the long-term persistence of SB623 cells after subretinal injection, and show that the transplanted SB623 cells were able to prevent death of photoreceptor cells.

What is claimed is:

1. A method for increasing electrical activity of a photoreceptor cell in a subject, the method comprising administering, to the subject, cells descended from marrow adherent stem cells (MASCs) that have been engineered to express an exogenous Notch intracellular domain.

2. The method of claim 1, wherein the cells are transplanted into the eye of the subject.

3. The method of claim 2, wherein the transplantation is intravitreal.

4. The method of claim 2, wherein the transplantation is subretinal.

5. The method of claim 1, wherein the electrical activity is increased in an individual having retinitis pigmentosa.

6. The method of claim 1, wherein the electrical activity is increased in an individual having age-related macular degeneration (AMD).

7. A method for preventing loss of cells of the outer nuclear layer of the retina in a subject, the method comprising administering, to the subject, cells descended from marrow adherent stem cells (MASCs) that have been engineered to express an exogenous Notch intracellular domain.

8. The method of claim 7, wherein the cells descended from marrow adherent stem cells are transplanted into the eye of the subject.

9. The method of claim 8, wherein the transplantation is intravitreal.

10. The method of claim 8, wherein the transplantation is subretinal.

11. The method of claim 7, wherein the loss of cells of the outer nuclear layer of the retina is prevented in an individual having retinitis pigmentosa.

12. The method of claim 7, wherein loss of cells of the outer nuclear layer of the retina is prevented in an individual having age-related macular degeneration (AMD).

13. A method for enhancing transmission of visual signals from the retina to the visual cortex in a subject, the method comprising administering, to the subject, cells descended from marrow adherent stem cells (MASCs) that have been engineered to express an exogenous Notch intracellular domain.

14. The method of claim 13, wherein the cells are transplanted into the eye of the subject.

15. The method of claim 14, wherein the transplantation is intravitreal.

16. The method of claim 14, wherein the transplantation is subretinal.

17. The method of claim 13, wherein the transmission of visual signals from the retina to the visual cortex is enhanced in an individual having retinitis pigmentosa.

18. The method of claim 13, wherein transmission of visual signals from the retina to the visual cortex is enhanced in an individual having age-related macular degeneration (AMD).

* * * * *